United States Patent [19]
Whitmer

[11] 3,947,699
[45] Mar. 30, 1976

[54] APPARATUS FOR SELECTING A PREDETERMINED PORTION OF AN ANALOG SIGNAL AND GATING IT TO AN OUTPUT

[75] Inventor: Delbert O. Whitmer, Ames, Iowa

[73] Assignee: Iowa State University Research Foundation, Inc., Ames, Iowa

[22] Filed: Aug. 29, 1974

[21] Appl. No.: 501,509

[52] U.S. Cl.............. 307/235 N; 328/147; 328/114; 307/236; 307/263
[51] Int. Cl.² ......................................... H03K 5/20
[58] Field of Search............... 307/235 N, 236, 263; 328/151, 146, 114, 147

[56] References Cited
UNITED STATES PATENTS

| | | |
|---|---|---|
| 3,524,075 | 8/1970 | Matthews et al. ............... 328/151 X |
| 3,553,595 | 1/1971 | Walsh ............................. 307/235 N |
| 3,602,825 | 8/1971 | Senior............................. 328/151 X |
| 3,875,516 | 4/1975 | Thomas .............................. 328/146 |

*Primary Examiner*—John S. Heyman
*Attorney, Agent, or Firm*—Dawson, Tilton, Fallon & Lungmus

[57] ABSTRACT

An input signal is fed to one signal lead of a gate or switch and, at the same time, to circuitry for initiating and terminating the conduction period of the gate. A bistable circuit is controlled by the initiation and termination circuitry, and it feeds the control lead of the gate to couple a predetermined portion of the input analog signal to an output. The initiation and termination circuitry provides for independent selection of the polarity of the slope and the amplitude of the incoming waveform in defining the start and end points on the incoming waveform for coupling to the output.

3 Claims, 3 Drawing Figures

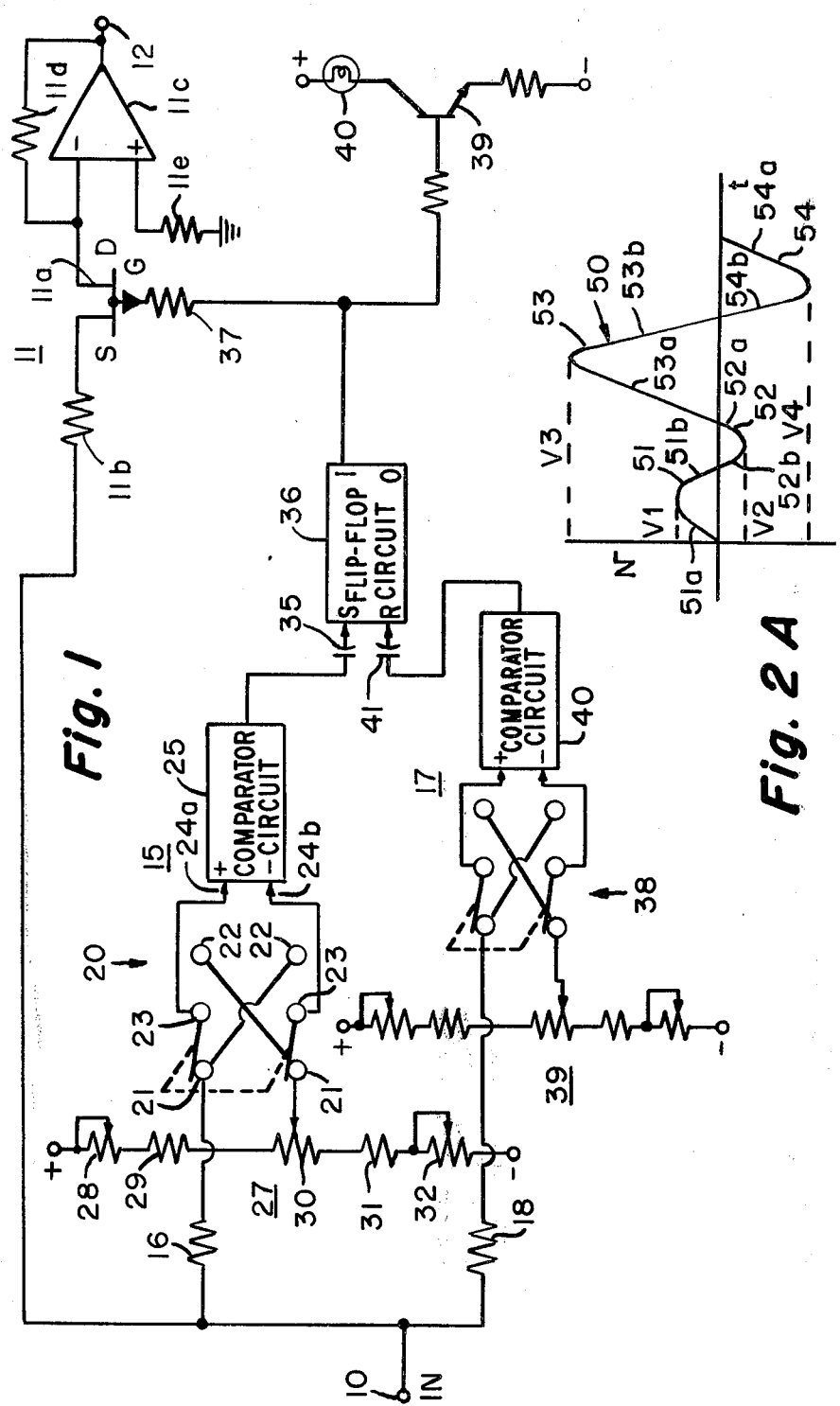
Fig. 1
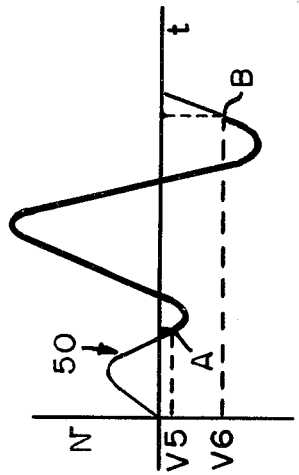
Fig. 2A
Fig. 2B

APPARATUS FOR SELECTING A PREDETERMINED PORTION OF AN ANALOG SIGNAL AND GATING IT TO AN OUTPUT

BACKGROUND AND SUMMARY

The present invention relates to a system for selecting a predetermined portion of an input analog waveform and coupling only the selected portion to the output. Settings are incorporated for selecting the initiation or start point of the selected portion of the input waveform to be either on a positive or a negative slope, and an additional setting is provided for independent adjustment of the amplitude at which the selection commences. This amplitude may be either positive or negative. Similarly, settings are provided so that the selected portion of the input analog waveform may be terminated on either a positive or a negative slope, and again, independent settings determine the amplitude of the termination or end point of the selected portion of the input waveform.

The principal object of the present system is to isolate a preselected portion of an input analog waveform. Such waveform may be, but not necessarily is periodic; and it may be either coherent or non-coherent such as a pulse. The isolated portion of the analog waveform may then be subjected to further analysis or study.

The present invention has been used to study the pressure wave of the left ventricle of the heart, which wave was recorded from a standard cardiac pressure transducer.

A typical or normal left ventricle pressure wave has an origin in the range of −5 to +5mmHg and rises rapidly to 100mmHg or more. It was originally desired to isolate the wave segment between +15mmHg and +75mmHg. This information is then fed to an integrator which accumulated information for 1 minute—that is, for 60 to 80 heartbeats. From this information, and knowing the total number of heartbeats, a convenient estimation could be made and the average time required for the early phase of heart contraction. This, in turn, permitted a study to be made of the average contraction velocity under different conditions such as heart failure, drug influences, etc.

Other features and advantages of the present invention will be apparent to persons skilled in the art from the following detailed description of a preferred embodiment accompanied by the attached drawing.

THE DRAWING

FIG. 1 is a circuit schematic diagram, partly in functional block form, of a system construction according to the present invention; and FIGS. 2A and 2B are idealized graphs of an arbitrary analog waveform which illustrate the utilization of the present invention.

DETAILED DESCRIPTION

Referring first to FIG. 1, reference numeral 10 designates an input terminal to which the input repetitive analog signal is coupled. The input analog signal is fed to a gating or switching circuitry generally designated by reference numeral 11 which, in the illustrated embodiment, includes a semi-conductor switch in the form of a Field Effect Transistor 11a, having a drain terminal D, a source terminal S and a gate terminal G (which is the control terminal for switching). The input analog signal is coupled via a resistor 11b to the drain terminal D, and the selected portion of the input analog signal desired to be further analyzed is coupled via the source terminal S of the semiconductor switch 11a to the negative input terminal of an operational amplifier 11c which feeds an output terminal 12.

A feedback resistor 11d is connected between the output terminal and the negative input terminal of the operational amplifier 11c. The positive input terminal is connected to the ground through a resistor 11e. Certain advantages are derived from this switching circuit arrangement which will be described below.

The input analog signal is also connected to initiation circuitry generally designated 15 by means of a first coupling resistor 16, and to termination circuitry generally designated by reference numeral 17 by means of a second coupling resistor designated 18. Referring first to the initiation circuitry 15, its function is to cause the gate or switch 11 to conduct responsive to: (a) a preselected slope polarity (positive or negative) of the input analog waveform, and (b) a preselected amplitude which may be either positive or negative.

The coupling resistor 16 is connected to a double-pole, double-throw switch generally designated by reference numeral 20, and having a first pair of input terminals 21, a second pair of input terminals 22 cross-connected to the input terminals 21, and a pair of output terminals 23. The function of the switch 20 is to select the slope polarity of the input waveform (positive for increasing signal or negative for decreasing signal) at which it is desired to initiate conducting of the switch 11; hence, it is sometimes referred to as a slope polarity selection switch or means.

The output or movable terminals 23 of the switch 20 are connected directly to the input teminals 24a and 24b respectively of a comparator circuit 25 in the polarity shown.

The comparator circuit 25 is of conventional design, and is well known in the art. It operates in a mode such that its output signal is a logic level—i.e., it is either relatively high or relatively low. The output signal is relatively high if the input signal on terminal 24a is more positive than the input signal at the terminal 24d. The output signal is relatively low if the signal at input terminal 24b is more positive than the signal at input 24a.

As mentioned, the input terminals 21 and 22 of the switch 20 are interconnected such as to reverse polarity of the output signal from the switch depending upon the position of the movable contacts which are directly connected to the output terminals 23. In either case, one input to the switch 20 is received from the system input terminal 10 by means of the coupling resistor 16. The other input terminal is received from a reference voltage network generally designated by reference numeral 27.

The reference voltage network 27 includes a number of resistors which are connected between positive and negative voltage supplies, which are of the same magnitude. Connected between the positive and negative terminals, and in series, are a variable resistor 28, a fixed resistor 29, a potentiometer 30, a second fixed resistor 31, and a second variable resistor 32. The fixed resistor 29 and 31 are used to limit current. The variable resistors 28 and 32 are internal of the apparatus and used to set the range of the reference voltage relative to the positive and negative supply levels that are available. The potentiometer 30 is used to set the reference voltage for the comparator circuit 25.

The output of the comparator circuit 25 is coupled through a differentiating capacitor 35 to the set, S, input of a flip-flop circuit 36.

Turning now to the termination circuitry 17, it is similar to the initiation circuitry 15 disclosed above, and it need not be discussed in much detail for a complete understanding of the invention. Briefly, it includes a double-pole, double-throw slope polarity selection switch 38 which has one input connected to the input terminal 10 via resistor 18, and a second input connected to a resistive reference voltage network generally designated 39 and similar to the previously described network 27. The output terminals of the slope polarity selection switch 38 are connected to the input terminals of the comparator circuit 40, the output of which is coupled through a differentiating capacitor 41 to the reset input, R, of the flip-flop circuit 36.

The 1 output of the flip-flop circuit 36 is connected to the gate control lead G of the FET 11a by means of a resistor 37.

Also connected to the output of the flip-flop circuit 36 is a lamp driver transistor 39, in the collector circuit of which is a signal lamp 40. The signal lamp 40 is lit whenever the input analog signal is being coupled to the output of the system.

Preferably, the potentiometer 30 in the reference voltage network 27 and the corresponding variable resistor in the reference voltage network 39 are 10-turn potentiometers which are well known in the art. This offers a wide range of selection and increases the accuracy of the trigger levels. In the positions shown in the drawing, slope polarity selection switches 20, 38 will provide selection on positive slopes of the input signal; and in the other position, they will provide selection on a negative slope.

OPERATION

Referring now to FIG. 2A, there is shown an idealized waveform, generally designated by reference numeral 50 and assumed to be periodic or at least repetitive. It is illustrated merely to demonstrate the operation of the system described above. The same waveform is reproduced in FIG. 2B, and the darkened portion there represents that portion of the input waveform which is selected and coupled to the output 12. That is, the start point is designated A, and the termination point is designated B in FIG. 2B between these two points the output voltage is at a signal level representative of the input signal. At all other times the output voltage is at ground.

It will be observed that the waveform 50 has a first positive cusp 51, followed by a first negative cusp 52, a second positive cusp 53, and a second negative cusp 54. In FIGS. 2A and 2B, the abscissa is time and the ordinate is voltage.

The cusp 51 has a peak indicated at V1, and it includes a positive slope 51a and a negative slope 51b. Similarly, the cusp 52 has a negative maximum V2, a positive slope 52a, and a negative slope 52b. Similarly, the cusp 53 has a positive maximum V3, a positive slope designated 53a, and a negative slope designated 53b. Finally, the negative cusp 54 has a negative maximum V4, a positive slope 54a, and a negative slope 54b.

If it is desired to initiate the selection of the input waveform on the slope 51a, then the switch 20 is turned to the position shown in the drawing (a positive slope polarity selection) and potentiometer 30 is turned to the desired positive magnitude which, it will be observed, will be less than the magnitude V1. The dial settings on the variable resistors are calibrated, of course. If it is desired to select a start point on the slope 51b, but at the same amplitude or magnitude, only the switch 20 need be thrown.

If it is desired to initiate the selection of the input waveform on the slope 52a, the switch 20 is reversed from the position illustrated, and the potentiometer 30 is set to the desired negative level. Following through on this selection, it will be observed that as the input waveform follows along on the portion 52a, and goes below the level of the selected reference voltage, then the input 24b of the comparator circuit 25 will be less than the voltage from the reference voltage network 27 at the input 24a, and the output of the comparator circuit 25 will go positive to trigger the flip-flop 36, the output of which will cause the FET 11a to conduct because the gate terminal G will be positive.

The high input impedance of the operational amplifier 11c and the feedback causes the negative input terminal to act as a summing junction; hence, the voltage drop across the S and D terminals of the FET 11a remains near zero. This is advantageous because the switching can occur at various levels.

It will be observed that if the switch 20 is in the position illustrated and the magnitude of the reference voltage is set between the positions V1 and V3, then the initiation point will occur on the slope 53a.

Referring now to FIG. 2B, if it is desired to select the portion of the input waveform 50 which is shown in heavier line, and defined by the start point A and the termination point B, then the start slope polarity selection switch 20 is set to the reverse position from that illustrated, and the termination slope polarity selection switch 38 is left in the position illustrated (so as to terminate on a positive slope). The reference voltage network 27 is adjusted to generate a reference voltage which is negative and of the level indicated at V5 in 2B. Similarly, the reference voltage network 39 is adjusted to generate a voltage represented by the negative level V6. The width of the voltage pulse on the gate terminal D of the semiconductor switch 11a will, of course, vary in time according to the selection parameters indicated above.

Having thus described in detail a preferred embodiment of the invention, persons skilled in the art will be able to modify certain of the circuitry which has been illustrated, and to substitute equivalent elements for those disclosed while continuing to practice the principle of the invention; and it is, therefore, intended that all such modifications and substitutions be covered as they are embraced within the spirit and scope of the appended claims.

I claim:

1. Apparatus for selecting a predetermined portion of an input signal and for coupling said portion to an output while controlling the length of the selected portion comprising:

controlled gate circuit means having a first signal terminal connected to receive said input signal, a second signal terminal connected to said output for coupling a selected portion of said input signal thereto, and a control terminal;

initiation circuit means responsive to said input signal for generating a start signal including first comparator circuit means having first and second inputs, first settable circuit means for generating a first reference voltage of predetermined magnitude and polarity, first slope polarity selection circuit means for coupling said first reference voltage and said input signal to said first and second inputs of said first comparator circuit means;

termination circuit means for generating a termination signal including second comparator circuit means having first and second inputs, second settable circuit means for generating a second reference voltage of predetermined magnitude and polarity, second slope polarity selection circuit means for coupling said second reference voltage and said input signal to said first and second inputs of said second comparator circuit means; and bistable circuit means responsive to said start signal and said termination signal and feeding the control terminal of said switch means for causing said switch means to conduct in response to said start signal and for causing said switch to open in response to said termination signal; whereby said start and termination signals may be set to occur independently either on a positive or a negative slope of said input signal and at a desired voltage level.

2. The system of claim 1 wherein said bistable circuit means includes a capacitor in series with each input terminal whereby said bistable circuit means changes state only in response to changes in the outputs of said first and second comparator circuit means.

3. The apparatus of claim 1 wherein said switch means comprises a switching transistor and operational amplifier means having said transistor connected in circuit with one input terminal thereof and including resistive feedback means connected between said one input terminal and said output terminal.

* * * * *